(12) United States Patent
Sillerström et al.

(10) Patent No.: US 11,147,721 B2
(45) Date of Patent: Oct. 19, 2021

(54) ABSORBENT ARTICLE AND METHOD FOR MANUFACTURING AN ABSORBENT ARTICLE

(71) Applicant: Essity Hygiene and Health Aktiebolag, Gothenburg (SE)

(72) Inventors: Filip Sillerström, Gothenburg (SE); Helena Corneliusson, Gothenburg (SE); Therese Hermansson, Jonsered (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/757,656

(22) PCT Filed: Dec. 21, 2017

(86) PCT No.: PCT/SE2017/000051
§ 371 (c)(1),
(2) Date: Apr. 20, 2020

(87) PCT Pub. No.: WO2019/125228
PCT Pub. Date: Jun. 27, 2019

(65) Prior Publication Data
US 2020/0323709 A1    Oct. 15, 2020

(51) Int. Cl.
*A61F 13/532* (2006.01)
*A61F 13/15* (2006.01)
(Continued)

(52) U.S. Cl.
CPC .... *A61F 13/5323* (2013.01); *A61F 13/15203* (2013.01); *A61F 13/15739* (2013.01);
(Continued)

(58) Field of Classification Search
CPC combination set(s) only.
See application file for complete search history.

(56) References Cited

U.S. PATENT DOCUMENTS 5,330,456 A * 7/1994 Robinson .............. A61F 13/533
                                                    604/358
5,622,734 A    4/1997 Clark et al.
(Continued)

FOREIGN PATENT DOCUMENTS

CN    102770592 A    11/2012
CN    103596534 A    2/2014
(Continued)

OTHER PUBLICATIONS

International Search Report (PCT/ISA/210) and Written Opinion (PCT/ISA/237) dated Oct. 10, 2018, by the Swedish Patent Office as the International Searching Authority for International Application No. PCT/SE2018/050383.
(Continued)

*Primary Examiner* — Michele M Kidwell
(74) *Attorney, Agent, or Firm* — Buchanan Ingersoll & Rooney P.C.

(57) ABSTRACT

An absorbent article comprises an absorbent core sandwiched between a liquid-permeable topsheet and a liquid-impermeable backsheet. The article comprises front, back and crotch portions. The absorbent core comprises an absorbent component having a width in the transversal direction and the absorbent component is enclosed by a core cover comprising an upper side and a lower side. Two channel sealings extend along the longitudinal axis in the crotch portion for joining the upper and lower side of the core cover. A core cover, which is arranged around the absorbent component, defines and limits an expansion space for the centre segment so that the centre segment is prevented from reaching complete expansion to the second volume on wetting, and the ratio of the first width of the centre segment and the width of the absorbent component, in dry condition, is 0.25-0.45.

21 Claims, 4 Drawing Sheets

(51) Int. Cl.
*A61F 13/49* (2006.01)
*A61F 13/53* (2006.01)
(52) U.S. Cl.
CPC ............ *A61F 13/49011* (2013.01); *A61F 2013/15406* (2013.01); *A61F 2013/49092* (2013.01); *A61F 2013/530007* (2013.01); *A61F 2013/530481* (2013.01)

(56) References Cited

U.S. PATENT DOCUMENTS

| | | | |
|---|---|---|---|
| 6,102,900 A * | 8/2000 | Roessler | A61F 13/49017 604/385.24 |
| 6,563,013 B1 | 5/2003 | Murata | |
| 9,132,046 B2 | 9/2015 | Glaug et al. | |
| 9,974,698 B2 | 5/2018 | Jackels | |
| 10,071,000 B2 | 9/2018 | Umemoto et al. | |
| 10,149,788 B2 | 12/2018 | Kreuzer et al. | |
| 10,561,546 B2 | 2/2020 | Rosati et al. | |
| 10,806,642 B2 | 10/2020 | Tagomori et al. | |
| 2001/0014797 A1 | 8/2001 | Suzuki et al. | |
| 2003/0060791 A1 | 3/2003 | Drevik | |
| 2004/0127871 A1 | 7/2004 | Odorzynski et al. | |
| 2004/0138633 A1 | 7/2004 | Mishima et al. | |
| 2004/0243078 A1 | 12/2004 | Guidotti et al. | |
| 2006/0276767 A1 | 12/2006 | Ueminami et al. | |
| 2007/0093164 A1 | 4/2007 | Nakaoka | |
| 2007/0142802 A1 | 6/2007 | Suzuki | |
| 2008/0119810 A1 | 5/2008 | Kuroda et al. | |
| 2008/0132864 A1 | 6/2008 | Lawson et al. | |
| 2009/0036854 A1 * | 2/2009 | Guidotti | A61F 13/4751 604/369 |
| 2009/0088718 A1 | 4/2009 | Toyoshima et al. | |
| 2009/0270825 A1 | 10/2009 | Wciorka et al. | |
| 2010/0168700 A1 | 7/2010 | Schmidt et al. | |
| 2010/0262099 A1 | 10/2010 | Klofta | |
| 2010/0268183 A1 | 10/2010 | Een et al. | |
| 2011/0250413 A1 | 10/2011 | Lu et al. | |
| 2012/0143164 A1 | 6/2012 | Frank et al. | |
| 2012/0296301 A1 | 11/2012 | Lawson et al. | |
| 2012/0312491 A1 | 12/2012 | Jackels et al. | |
| 2012/0316526 A1 | 12/2012 | Rosati et al. | |
| 2012/0316528 A1 | 12/2012 | Kreuzer et al. | |
| 2012/0316529 A1 | 12/2012 | Kreuzer et al. | |
| 2012/0316530 A1 | 12/2012 | Armstrong-Ostle et al. | |
| 2012/0323195 A1 | 12/2012 | Ehrnsperger et al. | |
| 2012/0325408 A1 | 12/2012 | Hundorf et al. | |
| 2013/0138070 A1 | 5/2013 | Drevik | |
| 2013/0231622 A1 | 9/2013 | Dieringer et al. | |
| 2013/0240123 A1 | 9/2013 | Lasko et al. | |
| 2014/0005625 A1 | 1/2014 | Wirtz et al. | |
| 2014/0027066 A1 | 1/2014 | Jackels et al. | |
| 2014/0088535 A1 | 3/2014 | Xu et al. | |
| 2014/0163500 A1 | 6/2014 | Roe et al. | |
| 2014/0163503 A1 | 6/2014 | Arizti et al. | |
| 2014/0163506 A1 | 6/2014 | Roe et al. | |
| 2014/0163511 A1 | 6/2014 | Roe et al. | |
| 2014/0324007 A1 | 10/2014 | Hundorf et al. | |
| 2014/0324008 A1 | 10/2014 | Hundorf et al. | |
| 2014/0371701 A1 | 12/2014 | Bianchi et al. | |
| 2015/0032073 A1 * | 1/2015 | Noda | A61F 13/4756 604/385.101 |
| 2015/0038931 A1 | 2/2015 | Kreuzer et al. | |
| 2015/0051568 A1 | 2/2015 | Sakaguchi et al. | |
| 2015/0065975 A1 | 3/2015 | Roe et al. | |
| 2015/0065976 A1 | 3/2015 | Roe et al. | |
| 2015/0080821 A1 | 3/2015 | Peri et al. | |
| 2015/0173968 A1 | 6/2015 | Joseph | |
| 2015/0245954 A1 | 9/2015 | Varga et al. | |
| 2015/0374562 A1 | 12/2015 | Hippe et al. | |
| 2016/0058630 A1 | 3/2016 | Roe et al. | |
| 2016/0058632 A1 | 3/2016 | Lawson et al. | |
| 2016/0081862 A1 | 3/2016 | Mason et al. | |
| 2016/0206482 A1 | 7/2016 | Nishikawa et al. | |
| 2016/0206485 A1 | 7/2016 | Seitz et al. | |
| 2016/0235595 A1 | 8/2016 | Ehrnsperger et al. | |
| 2016/0235604 A1 * | 8/2016 | Ehrnsperger | A61F 13/494 |
| 2016/0270971 A1 | 9/2016 | Raycheck et al. | |
| 2016/0270982 A1 | 9/2016 | Raycheck et al. | |
| 2016/0270986 A1 | 9/2016 | Stiehl et al. | |
| 2016/0270987 A1 | 9/2016 | Stiehl et al. | |
| 2016/0331602 A1 | 11/2016 | Bianchi et al. | |
| 2016/0346136 A1 | 12/2016 | Strasemeier et al. | |
| 2017/0057157 A1 | 3/2017 | Lebowitz | |
| 2017/0079853 A1 | 3/2017 | Willhaus et al. | |
| 2017/0079857 A1 | 3/2017 | Willhaus et al. | |
| 2017/0172810 A1 | 6/2017 | Van De Maele | |
| 2018/0021187 A1 | 1/2018 | Nishikawa et al. | |
| 2018/0049924 A1 | 2/2018 | Van De Maele | |
| 2018/0049925 A1 | 2/2018 | Van De Maele | |
| 2019/0038477 A1 | 2/2019 | Jackels et al. | |
| 2020/0078229 A1 | 3/2020 | Van Ingelgem et al. | |
| 2020/0337909 A1 * | 10/2020 | Sillerstrom | A61F 13/15203 |
| 2020/0375822 A1 * | 12/2020 | Sillerstrom | A61F 13/539 |

FOREIGN PATENT DOCUMENTS

| | | |
|---|---|---|
| CN | 103607990 A | 2/2014 |
| CN | 203988675 U | 12/2014 |
| CN | 104837458 A | 8/2015 |
| CN | 204671400 U | 9/2015 |
| CN | 105816277 A | 8/2016 |
| CN | 107249529 A | 10/2017 |
| CN | 107405240 A | 11/2017 |
| DE | 29513199 U1 | 2/1996 |
| DE | 202012013564 U | 12/2017 |
| DE | 202012013571 U1 | 12/2017 |
| DE | 202013012614 U1 | 12/2017 |
| DE | 202013012616 U1 | 12/2017 |
| DE | 202013012617 U1 | 12/2017 |
| DE | 202017005496 U1 | 1/2018 |
| DE | 202017005950 U1 | 4/2018 |
| DE | 202017005952 U1 | 4/2018 |
| DE | 202017005956 U1 | 4/2018 |
| EP | 0813850 A2 | 12/1997 |
| EP | 0958801 A1 | 11/1999 |
| EP | 1110528 A2 | 6/2001 |
| EP | 1 116 479 A2 | 7/2001 |
| EP | 1880700 A1 | 1/2008 |
| EP | 1679055 B1 | 4/2010 |
| EP | 2444046 A1 | 4/2012 |
| EP | 2740449 A1 | 6/2014 |
| EP | 2740450 A1 | 6/2014 |
| EP | 2740452 A1 | 6/2014 |
| EP | 2886092 A1 | 6/2015 |
| EP | 2886093 A1 | 6/2015 |
| EP | 2905000 A1 | 8/2015 |
| EP | 2949299 A1 | 12/2015 |
| EP | 2949300 A1 | 12/2015 |
| EP | 2949301 A1 | 12/2015 |
| EP | 2949302 A1 | 12/2015 |
| EP | 2979671 A1 | 2/2016 |
| EP | 2717823 B1 | 5/2016 |
| EP | 3058915 A1 | 8/2016 |
| EP | 3058918 A1 | 8/2016 |
| EP | 3111903 A1 | 1/2017 |
| EP | 3167858 A1 | 5/2017 |
| EP | 3167859 A1 | 5/2017 |
| EP | 3238676 A1 | 11/2017 |
| EP | 3338751 A1 | 6/2018 |
| EP | 3348246 A1 | 7/2018 |
| EP | 3403626 A1 | 11/2018 |
| EP | 3403632 A1 | 11/2018 |
| EP | 3453368 A1 | 3/2019 |
| FR | 2604867 A1 | 4/1988 |
| GB | 2518174 A | 3/2015 |
| JP | 2008119081 A | 5/2008 |
| JP | 2009-536865 A | 10/2009 |
| JP | 2011125360 A | 6/2011 |
| JP | 2013102888 A | 5/2013 |
| JP | 3201606 U | 11/2015 |
| JP | 2016112359 A | 6/2016 |
| JP | 2016112404 A | 6/2016 |
| RU | 2260414 C2 | 9/2005 |

(56) References Cited

FOREIGN PATENT DOCUMENTS

| RU | 2379014 C2 | | 1/2010 | |
|---|---|---|---|---|
| WO | 0217842 A2 | | 3/2002 | |
| WO | 0217843 A2 | | 3/2002 | |
| WO | 02056812 A2 | | 7/2002 | |
| WO | 2004006818 A1 | | 1/2004 | |
| WO | 2005065611 A1 | | 7/2005 | |
| WO | 2007046974 A1 | | 4/2007 | |
| WO | 2009001711 A1 | | 12/2008 | |
| WO | 2009128757 A1 | | 10/2009 | |
| WO | 2011105109 A1 | | 9/2011 | |
| WO | 2011106663 A1 | | 9/2011 | |
| WO | 2012014436 A1 | | 2/2012 | |
| WO | 2014004439 A1 | | 1/2014 | |
| WO | 2014/093310 | * | 9/2014 | ........... A61F 13/475 |
| WO | 2016065000 A1 | | 4/2016 | |
| WO | 2016147760 A1 | | 9/2016 | |
| WO | 2016189759 A1 | | 12/2016 | |
| WO | 2017053035 A1 | | 3/2017 | |
| WO | 2017053036 A1 | | 3/2017 | |
| WO | 2017189151 A1 | | 11/2017 | |
| WO | 2017189152 A1 | | 11/2017 | |
| WO | 2018006027 A1 | | 1/2018 | |
| WO | 2018210751 A1 | | 11/2018 | |
| WO | 2018210752 A1 | | 11/2018 | |
| WO | 2018210753 A1 | | 11/2018 | |
| WO | 2018210754 A1 | | 11/2018 | |
| WO | 2018210756 A1 | | 11/2018 | |
| WO | 2018210757 A1 | | 11/2018 | |
| WO | 2018210758 A1 | | 11/2018 | |
| WO | 2019005666 A1 | | 1/2019 | |
| WO | 2019048397 A1 | | 3/2019 | |
| WO | 2019125227 A1 | | 6/2019 | |
| WO | 2019125228 A1 | | 6/2019 | |

OTHER PUBLICATIONS

International Search Report (PCT/ISA/210) and Written Opinion (PCT/ISA/237) dated Mar. 1, 2019, by the Swedish Patent Office as the International Searching Authority for International Application No. PCT/SE2018/051361.
International Search Report (PCT/ISA/210) dated Oct. 10, 2018, by the Swedish Patent Office as the International Searching Authority for International Application No. PCT/SE2017/000053.
International Search Report (PCT/ISA/210) dated Oct. 10, 2018, by the Swedish Patent Office as the International Searching Authority for International Application No. PCT/SE2017/000055.
International Search Report (PCT/ISA/210) dated Sep. 3, 2018, by the Swedish Patent Office as the International Searching Authority for International Application No. PCT/SE2017/000050.
International Search Report (PCT/ISA/210) dated Sep. 3, 2018, by the Swedish Patent Office as the International Searching Authority for International Application No. PCT/SE2017/000051.
International Search Report (PCT/ISA/210) dated Sep. 3, 2018, by the Swedish Patent Office as the International Searching Authority for International Application No. PCT/SE2017/000054.
International Search Report (PCT/ISA/210) dated Sep. 7, 2018, by the Swedish Patent Office as the International Searching Authority for International Application No. PCT/SE2017/000052.
Written Opinion (PCT/ISA/237) dated Oct. 10, 2018, by the Swedish Patent Office as the International Searching Authority for International Application No. PCT/SE2017/000053.
Written Opinion (PCT/ISA/237) dated Oct. 10, 2018, by the Swedish Patent Office as the International Searching Authority for International Application No. PCT/SE2017/000055.
Written Opinion (PCT/ISA/237) dated Sep. 3, 2018, by the Swedish Patent Office as the International Searching Authority for International Application No. PCT/SE2017/000050.
Written Opinion (PCT/ISA/237) dated Sep. 3, 2018, by the Swedish Patent Office as the International Searching Authority for International Application No. PCT/SE2017/000051.
Written Opinion (PCT/ISA/237) dated Sep. 3, 2018, by the Swedish Patent Office as the International Searching Authority for International Application No. PCT/SE2017/000054.
Written Opinion (PCT/ISA/237) dated Sep. 7, 2018, by the Swedish Patent Office as the International Searching Authority for International Application No. PCT/SE2017/000052.
Third Party Observation mailed on Apr. 3, 2020, by the Swedish Patent Office for International Application No. PCT/SE2017/000051.
Third Party Observation mailed on Apr. 7, 2020, by the Swedish Patent Office for International Application No. PCT/SE2017/000050.
Office Action (Decision on Grant) dated Nov. 23, 2020, by the Federal Service for Intellectual Property in Russian Patent Application No. 2020123924/03(041325) and an English Translation of the Office Action. (27 pages).
Office Action (Notification of the First Office Action) dated Oct. 19, 2020, by the China National Intellectual Property Administration (CNIPA) of the People's Republic of China in corresponding Chinese Patent Application No. 201780096125.0, and an English Translation of the Office Action. (14 pages).
Office Action (Notice of acceptance for patent application) dated Nov. 9, 2020 by the Australian Government—IP Australia in corresponding Australian Patent Application No. 2017443955. (3 pages).
Office Action (Decision on Grant) dated Sep. 28, 2020, by the Federal Service for Intellectual Property in Russian Patent Application No. 2020123912/03(041313) and an English Translation of the Office Action. (25 pages).
Office Action (Notification of the First Office Action) dated Nov. 13, 2020, by the China National Intellectual Property Administration (CNIPA) of the People's Republic of China in corresponding Chinese Patent Application No. 201780096151.3, and an English Translation of the Office Action. (9 pages).
Office Action (Notification of the First Office Action) dated Oct. 20, 2020, by the China National Intellectual Property Administration (CNIPA) of the People's Republic of China in corresponding Chinese Patent Application No. 201780096152.8, and an English Translation of the Office Action. (20 pages).
Office Action (Examinnation Report No. 2 for standard patent application) dated Mar. 10, 2021by the Australian Government—IP Australia in corresponding Australian Patent Application No. 2017443609. (5 pages).
Extended European Search Report dated Jul. 2, 2021, issued by the European Patent Office in corresponding European Application No. 17935259.6-1102, (7 pages).
Office Action (Notice of Reasons for Rejection) dated Aug. 24, 2021, by the Japanese Patent Office in corresponding Japanese Patent Application No. 2020-533296, and an English Translation of the Office Action. (14 pages).

* cited by examiner

ABSORBENT ARTICLE AND METHOD FOR MANUFACTURING AN ABSORBENT ARTICLE

TECHNICAL FIELD

The disclosure relates to an absorbent article comprising an absorbent core sandwiched between a liquid-permeable topsheet and a liquid-impermeable backsheet. The disclosure also relates to an absorbent core for an absorbent article, and a method for manufacturing an absorbent article of the above-mentioned type.

BACKGROUND

Wearable and disposable absorbent articles, for example in the form of diapers, incontinence garments, feminine garments and the like, are well known. Such articles are used to absorb, distribute and store various types of body exudates while providing a high level of comfort and sense of dryness to the wearer during use.

A conventional disposable absorbent article in the form of a diaper is normally designed with an absorbent core which is sandwiched between a topsheet and a backsheet. The article is arranged along a longitudinal axis and along a transversal axis which extends in a perpendicular direction in relation to the longitudinal axis. Furthermore, the article can be divided into a front portion, a back portion and a crotch portion.

The absorbent article will absorb body exudates when it is worn. A potential disadvantage which may occur when the absorbent article is in its wet condition is that the crotch portion may sag and hang down. This tendency for sagging is unwanted and may lead to insufficient comfort, fit and function of the article.

A previously known absorbent article of the above-mentioned kind is disclosed in the patent document US 2012/316528. This document shows a disposable diaper having an absorbent core which, according to an embodiment, comprises longitudinally extending and channels.

The purpose of the diaper is to provide good liquid handling properties and an increased flexibility and improved fit during use.

Even though the article disclosed in US 2012/316528 fulfills certain requirements related to liquid handling and fit, there is a need for further improvements.

SUMMARY

The present disclosure is based on the insight that the ability of an absorbent article such as for example a diaper, to avoid sagging in its wet condition during use, may be influenced by certain features of the article.

In accordance with the disclosure there is provided an absorbent article and a core.

An absorbent article comprising an absorbent core sandwiched between a liquid-permeable topsheet and a liquid-impermeable backsheet, said article being arranged along a longitudinal axis and a transversal axis extending in a perpendicular direction in relation to the longitudinal axis, said article comprising a front portion, a back portion and a crotch portion and said absorbent core comprises an absorbent component having a width (a3) in the transversal direction and the absorbent component is enclosed by a core cover comprising an upper side and a lower side wherein two channel sealings are extending along said longitudinal axis in said crotch portion for joining said upper and lower side of the core cover. The absorbent component has one centre segment having a first width (a1) between the channel sealings, and two side segments outside each channel sealing. The absorbent component is formed so that the total amount of absorbent material in the centre segment is generally equal to, or greater than, the total amount of absorbent material in each one of the side segments. The channel sealings and the centre segment are generally parallel to the longitudinal axis and the absorbent component is configured with an ability to expand on wetting and displaying a first volume in dry condition and a second volume in completely expanded wet condition, the second volume being greater than the first volume. The core cover which is arranged around the absorbent component constitutes volume-limiting means and defines and limits an expansion space for the centre segment so that the centre segment is prevented from reaching complete expansion to the second volume on wetting. Furthermore, the ratio of the first width (a1) of the centre segment and the absorbent component width (a3), in dry condition, is 0.25-0.45.

The disclosure provides certain advantages. The disclosure fulfills requirements on absorbent articles related to improved fit, comfort and function in its wet condition. It is provided an absorbent article in which the crotch portion, and in particular the central segment, may be configured with an increased stiffness as compared with the remaining parts of the absorbent core. The problem with sagging will gradually increase when the amount of liquid absorbed by the article is increased and the absorbent article, as defined in the present disclosure, is constructed so that the stiffness in the centre segment is gradually increased as a generally linear function to the amount of liquid absorbed by the article. In the beginning, when only a small amount of liquid has been absorbed, the problem with sagging is not a problem, and therefore the stiffness in the centre segment does not need to be high. However, when the amount of absorbed liquid increases, the problem with sagging will also increase, and so a higher stiffness in the centre segment is needed.

Furthermore, according to the present disclosure, the absorbent side segments will not, at least not to a substantial extent, increase its stiffness in wet condition. The absorbent side segments will ensure sufficient total absorbent capacity in the crotch portion without contributing to creating a stiff element along the whole width of the absorbent component. According to the present disclosure, an absorbent article is obtained having less problem with sagging while at the same time having sufficient absorption capacity in the crotch portion and also being comfortable to wear for the user.

The core cover enclosing the centre segment thus defines and limits the expansion space for the absorbent material in the centre segment. It is not necessary for the disclosure that the expansion space is completely closed around the centre segment, only that the swelling of the absorbent material in the centre segment is prevented in the desired swelling direction.

When defining that the total amount of absorbent material in the centre segment is generally equal to, or greater than the total amount of absorbent material in each one of the side segments, is meant that the total weight of the absorbent material in the centre segment is generally equal to, or greater than, the total weight of the absorbent material in each one of the side segments.

The ratio of the width of the centre segment and the absorbent component width, in dry condition, may be 0.30-0.40. The width of the centre segment in dry condition may be 25-35 mm, or 29-33 mm.

The centre segment may have a greater stiffness after wetting than in dry condition and thus forms a forming element in the absorbent article.

The thickness of the absorbent component in dry condition, measured with an applied pressure of 0.5 kPa, may be 3.0-5.5 mm or 4.0-5.0 mm.

The article may also have leg elastic elements extending along each longitudinal side edge of the absorbent article. The leg elastic elements may have a greater length in the longitudinal direction than the length of the channel sealings in the longitudinal direction.

The leg elastic elements are, in the longitudinal direction, extending also along a part of the front portion and the back portion. The leg elastic elements may have a greater extension in the back portion than in the front portion. The leg elastic elements together with the absorbent component comprising a centre segment and two side segments according to the present disclosure contribute to an improved fit of the article during use.

The ratio of the width of the centre segment ($a_1$) and the distance in the transversal direction between the leg elastics ($c_1$) may be 0.10-0.30, 0.15-0.25 or 0.18-0.22.

The article may also have a waist elastic element located in the back portion close to the back edge of the absorbent article. The waist elastic element, together with the leg elastic elements and the absorbent component comprising a centre segment and two side segments according to the present disclosure contribute to an improved fit of the article during use.

The absorbent component in the crotch portion may be configured so that 33-41 weight % of the absorbent material is in the centre segment and 25-33 weight % of the absorbent material is in each one of the side segments.

The absorbent material in the absorbent component may comprise pulp material and superabsorbent material. The absorbent material in the absorbent component, at least in the crotch portion, may be constituted by 50-100 weight % superabsorbent material and 0-50 weight % pulp material, or 70-100 weight % superabsorbent material and 0-30% pulp material.

The total absorbent capacity per cubic centimeter of the absorbent structure in dry condition may be at least 15 g/cm$^3$, or at least 25 g/cm$^3$ or at least 35 g/cm$^3$.

The pulp material may have a basis weight which is in the interval of 50-400 g/m$^2$ and the superabsorbent material may have a basis weight which is in the interval of 100-900 g/m$^2$.

The absorbent article may also comprise two side seams along the sides of said core, and each of the two side segments has a second width ($a_2$). Also a third width ($b_1$) is defined between the channel sealings and a fourth width ($b_2$) is defined between a channel sealing and the side seam. The ratio of the first width ($a_1$) and the third width ($b_1$) may be greater than the ratio of the second width ($a_2$) and the fourth width ($b_2$). The fact that the ratio of the of the first width and the third width is greater than the ratio of the second width and the fourth width means that the expansion space of the absorbent material in the centre segment will be less than the expansion space of the absorbent material in the side segments resulting in a centre segment which may be stiffer than the above-mentioned side segments when the article is in a wet condition. This stiffness of the centre segment will counteract the tendency for the crotch portion to sag during use.

The ratio of the first width ($a_1$) and the third width ($b_1$) may be in the interval 0.75-0.91 or 0.80-0.86 and the ratio of the second width ($a_2$) and the fourth width ($b_2$) may be in the interval 0.57-0.71 or 0.62-0.66. Said first, second, third and fourth widths may be configured so that $b_1 < b_2*2$ and $a_1 < a_2*2$.

Each channel sealing may have a length which is between 5-50%, 10-50% or 28-38% of the total length of the article.

Each channel sealing may have a length which is between 10-60%, 20-60% or 30-50%, of the length of the absorbent core.

The position of the channel sealings along the longitudinal direction of the article may be arranged so that the distance between the front edge of the article and the front edge of each channel is 15-40%, or 22-25%, of the total length of the article.

The core cover may be formed by a separate upper core cover layer and a separate lower core cover layer. However, the disclosure is not limited to a core cover comprising two separate core cover layers. The core cover may also be of one single material layer. The absorbent component may be enclosed by one core cover layer folded in two, or enclosed by a continuous core cover sheet, thereby providing upper and lower core cover sides for wrapping the absorbent component. The basis weight of the core cover material may be in the interval 5-20 g/m$^2$. The core cover material may be made of thermoplastic polymer material. The core cover material may be nonwoven material. The nonwoven material may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

The absorbent component may be constituted by one single absorbent component layer being wrapped in a core cover having an upper and lower side.

The absorbent core may be rectangular.

The channel sealings may be positioned within two corresponding channels which constitute sections of the absorbent core which are generally free from absorbent material.

The absorbent article may comprise at least one additive material in the form of a skin care composition. The skin care composition may be applied on the topsheet, at least on the surface above the side segments.

According to a further aspect of the absorbent article of the present disclosure comprises the absorbent article an absorbent core sandwiched between a liquid-permeable topsheet and a liquid-impermeable backsheet, said article being arranged along a longitudinal axis and a transversal axis extending in a perpendicular direction in relation to the longitudinal axis and said article defining a front portion, a back portion and a crotch portion, wherein said absorbent core comprises an absorbent component enclosed by a core cover comprising an upper side and a lower side, and a sealing arrangement for joining said upper and lower sides and comprising two channel sealings, in the crotch portion, defining a first channel sealing width and a second channel sealing width, and also comprising two side seams along the sides of said core, wherein a centre segment having a first width is defined in the absorbent component between the channel sealings and two side segments each having a second width are defined in the absorbent component outside each channel sealing. Furthermore, the absorbent component may be formed so that the total amount of absorbent material in the centre segment is generally equal to, or greater than, the total amount of absorbent material in each one of the side segments, that a third width is defined between the channel sealings and a fourth width is defined between a channel sealing and a side seam, and that the ratio of the first width and the third width is greater than the ratio of the second width and the fourth width.

The sealing arrangement may be constituted by a welding pattern which may be produced by means of a thermo and/or mechanical sealing method. The thermo and/or mechanical sealing may be ultrasonic welding or thermo sealing.

The welding pattern may comprise a plurality of welding spots being arranged in the form of a first row along the longitudinal axis wherein each welding spot extends along a first axis, being different from the longitudinal axis. Furthermore, a plurality of welding spots being arranged in the form of a second row along the longitudinal axis wherein each welding spot in the second row extends along a second axis, also being different from the longitudinal axis, and said first axis and second axis may define a first angle ($\alpha 1$) in relation to each other. Said first angle may be 45-130°, 45-100° or 45-70°. Also, said welding spots may be generally rectangular, oval or oblong. Said first axis may define a second angle with reference to said longitudinal axis which is within the interval 30-60°.

Each welding spot may have a length and a width and the length is greater than the width. Each welding spot, in the first row, may extend in its length direction along a first axis, and each welding spot, in the second row, may extend along a second axis.

The channel sealings may extend along said longitudinal axis in said crotch portion and may define a first effective channel sealing width and a second effective channel sealing width, and the side seams may define a third and fourth effective width, respectively, along said crotch portion and defining a fifth and sixth effective width, respectively, along said front portion and back portion; said effective widths being defined as the extension of said sealing arrangement in the transverse direction of the article, along any cross-section of the crotch portion, wherein the sum of said first to sixth effective widths in a transversal direction may be generally constant along said core.

There is also provided absorbent core for an absorbent article, said absorbent core comprising an absorbent component having a width (a3) in the transversal direction and the absorbent component is enclosed by a core cover comprising an upper side and a lower side wherein two channel sealings are extending along said longitudinal axis in said crotch portion for joining said upper and lower side of the core cover. The absorbent component has one centre segment having a first width (a1) between the channel sealings and two side segments outside each channel sealing. Furthermore, the absorbent component is formed so that the total amount of absorbent material in the centre segment is generally equal to, or greater than, the total amount of absorbent material in each one of the side segments and that the channel sealings and the centre segment are generally parallel to the longitudinal axis and that the absorbent component is configured with an ability to expand on wetting and displaying a first volume in dry condition and a second volume in completely expanded wet condition, the second volume being greater than the first volume, and the core cover, which is arranged around the absorbent component, constitutes volume-limiting means and defines and limits an expansion space for the centre segment so that the centre segment is prevented from reaching complete expansion to the second volume on wetting, and that the ratio of the width of the centre segment and the absorbent component width, in dry condition, is 0.25-0.45.

The disclosure may be varied within the scope of the appended claims. For example, the materials and dimensions used for the different layers forming the absorbent article 1 may be varied, as indicated above. The absorbent article may further include leg elastics, standing gathers, crotch and waist elastics, side panels, fastening systems etc. as known to the skilled man in the art and depending of the type of absorbent article intended.

BRIEF DESCRIPTION OF THE DRAWINGS

The disclosure will be described in greater detail below with reference to the figures shown in the appended drawings, wherein.

DETAILED DESCRIPTION

Different aspects of the present disclosure will be described more fully hereinafter with reference to the enclosed drawings. The embodiments disclosed herein can, however, be realized in many different forms and should not be construed as being limited to the aspects set forth herein.

Figure 1:
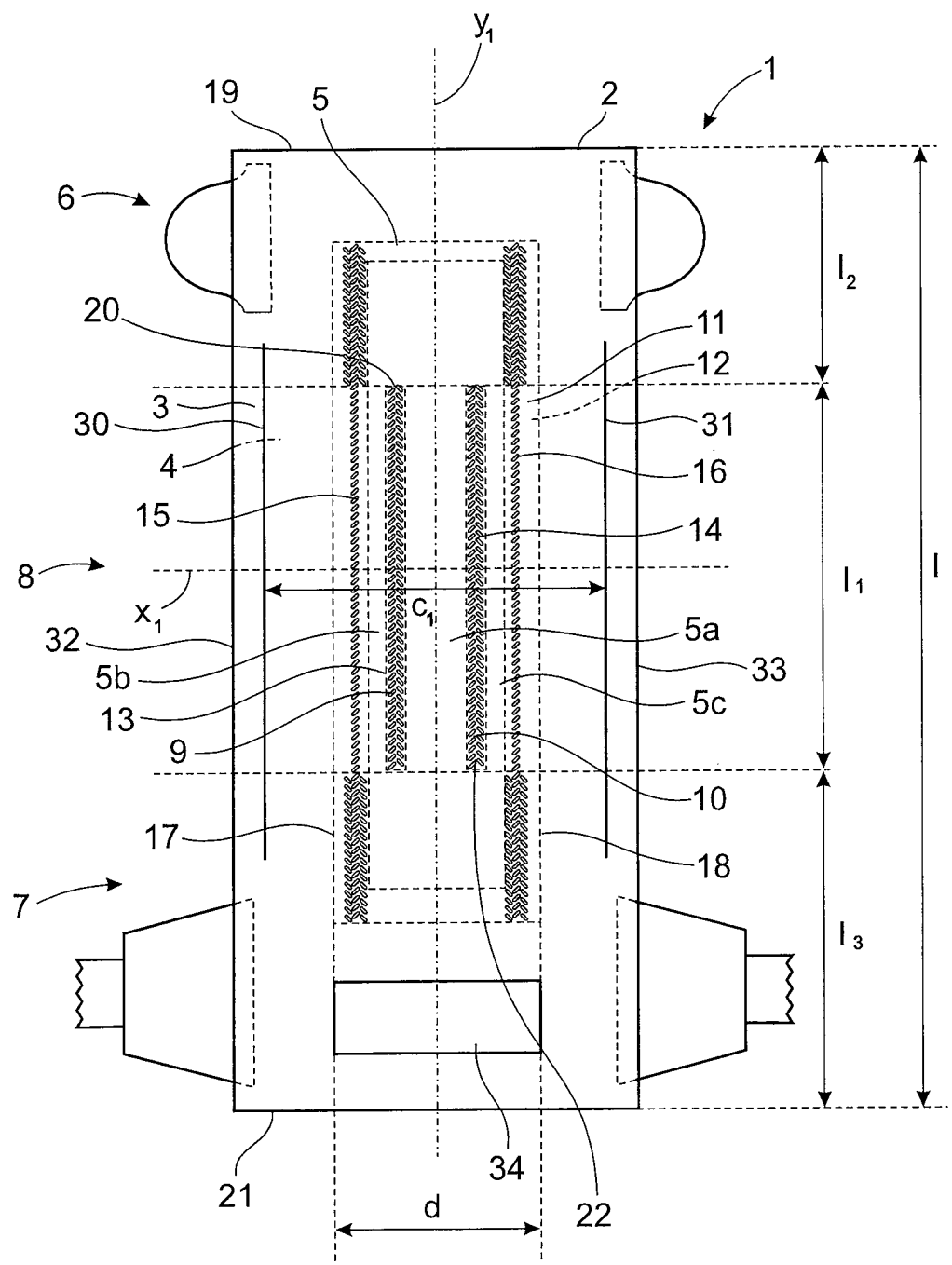
FIG. 1 shows a view from above of an absorbent article in the form of a diaper.

With initial reference to FIG. 1, there is shown a view from above of an absorbent article 1 in the form of a baby diaper. The absorbent article 1 is shown in FIG. 1 in an unfolded and flat state. Also, the absorbent article 1 is based on an absorbent structure for absorbing body exudates from a wearer to provide a dry and comfortable fit for the wearer.

As shown in FIG. 1, the absorbent article 1 comprises a liquid-permeable topsheet 3, a liquid-impermeable backsheet 4 an absorbent core 5 which is sandwiched between the topsheet 3 and the backsheet 4. The topsheet 3 is arranged at the surface of the article 1, i.e., at the side which is facing the wearer, whereas the backsheet 4 is arranged at the underside of the article 1. Furthermore, both the topsheet 3 and the backsheet 4 may extend laterally outside of the absorbent core 5 along the entire perimeter of the article 1.

The absorbent core shown in FIG. 1 has a rectangular design. However, the disclosure is not limited to this design but may be formed in generally any geometric form within the scope of the disclosure.

The topsheet 3, backsheet 4 and the absorbent core 5 may consist of any materials suitable for their purposes, as will be discussed in further detail below.

As shown in FIG. 1, the absorbent article 1 has a longitudinal extension along a longitudinal axis y1 and a transverse extension along a transverse axis x1, which is perpendicular to the longitudinal axis y1. Furthermore, the absorbent article 1 may be defined as being divided into a front portion 6, a back portion 7 and a crotch portion 8. The front 6 and back portions each having a waist edge 2. The front portion 6 is intended to be oriented in a direction towards the wearer's belly during use of the article 1.

Figure 2:
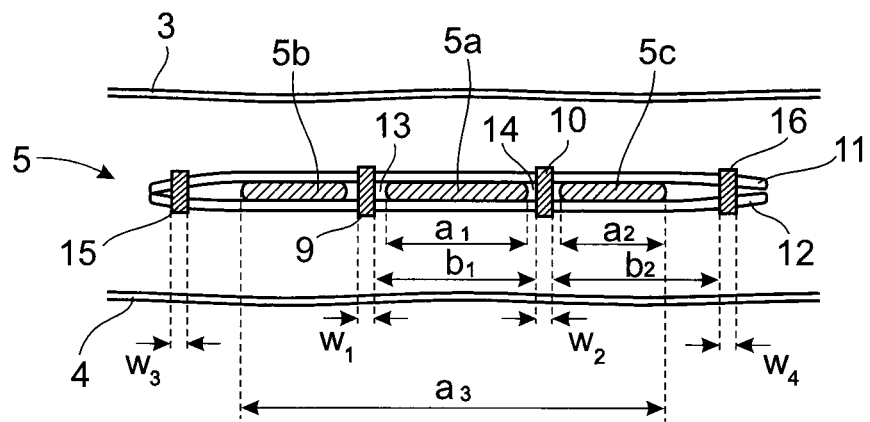
FIG. 2 shows a cross-sectional view of the diaper.

Furthermore, with reference to FIGS. 1 and 2, wherein FIG. 2 is a cross-sectional view of the absorbent article 1 along the transversal axis x1, it should be noted that the absorbent core 5 comprises an absorbent component 5a, 5b, 5c which is sandwiched between an upper core cover side 11 and a lower core cover side 12, and is formed with two longitudinally extending and generally straight channel sealings 9, 10 which are configured so as to join the upper core cover side 11 to the lower core cover side 12, see in particular FIG. 2, wherein the absorbent core 5 is sandwiched between said upper core cover side 11 and said lower core cover side 12. The disclosure is not limited to a core wrap comprising two core cover layers. The core cover may be of one single material layer. The absorbent component may be enclosed by one core cover layer folded in two, or enclosed by a continuous core cover sheet, thereby providing upper and lower core cover sides for wrapping the absorbent component.

The upper core cover side 11 and the lower core cover side 12 may be attached to each other by various technologies, for example, by thermo-mechanical bonding, such as thermo-sealing, ultrasonic bonding, an adhesive or adhesives, stitching or the like, or combinations of the same. According to FIGS. 1 and 2, the upper core cover side 11 and the lower core cover side 12 are attached to each other by ultrasonic welding.

The channel sealings 9, 10 are positioned along two corresponding channels 13, 14 which constitute sections of the absorbent core 5 which are not filled with absorbent material. This may be obtained through manufacturing the absorbent core 5 involving a mat forming process during which absorbent material is omitted from the areas which correspond to the channels 13, 14. In this manner, no absorbent material will be present in the channels 13, 14, i.e., where the channel sealings 9, 10 are arranged.

As shown in FIGS. 1 and 2, the absorbent core 5 may be divided into a centre segment 5a and two side segments 5b, 5c in the crotch portion 8. The two above-mentioned channels 13, 14, and the channel sealings 9, 10 will consequently be configured so that they separate the three segments 5a, 5b, 5c from each other along the crotch area 8. Also, the length l1 of each channel sealing 9, 10 may correspond to the length of the crotch portion 8 and may also be slightly less than the length of each channel 13, 14.

The absorbent core 5 may be generally rectangular and comprise two generally straight channel sealings 9, 10 which are generally parallel to said longitudinal axis y1 and define a first channel sealing width w1 and a second channel sealing width w2. The disclosure is not limited to a rectangular core 5 and generally straight channel sealings 9, 10, i.e., other geometrical configurations may occur. The channel sealings 9, 10 are positioned within the first channel 13 and the second channel 14, respectively, and are configured to attach the upper core cover side 11 to the lower core cover side 12.

Furthermore, the centre segment 5a is defined in the core 5 between the channel sealings 9, 10. Also, the two side segments 5b, 5c are defined in the core 5 outside each channel sealing 9, 10. More precisely, the first side segment 5b is positioned between the first channel sealing 9 and a first side seam 15, whereas the second side segment 5c is positioned between the second channel sealing 10 and a second side seam 16. The side seams 15, 16 are configured for joining the upper core cover side 11 to the lower core cover side 12, suitably by means of ultrasonic welding or other relevant technologies as described above with reference to the channel sealings 9, 10. Furthermore, the side seams 15, 16 extend along each side of the absorbent core 5, along a first side edge 17 and a second side edge 18 of the absorbent core 5.

As mentioned, the length l1 of the crotch portion 8 may be equal to the length of the channel sealings 9, 10, i.e., the channel sealings 9, 10 may extend along the crotch portion 8 only. However, the side seams 15, 16 may not just be positioned along the crotch portion 8 but also extend along the front portion 6 and the back portion 7. This will be described in detail below.

The absorbent article 1 also has leg elastic elements 30,31 extending along each longitudinal side edge 32,33 of the absorbent article 1. The leg elastic elements 30,31 have a greater length in the longitudinal direction than the length of the channel sealings 9,10 in the longitudinal direction.

The leg elastic elements 30, 31 are, in the longitudinal direction, extending also along a part of the front portion 6 and the back portion 7. The leg elastic elements 30, 31 have a greater extension in the back portion 7 than in the front portion 6.

The ratio of the width, a1, of the centre segment 5a and the distance in the transversal direction, c1, between the leg elastics 30,31, may be 0.10-0.30, 0.15-0.25 or 0.18-0.22.

The absorbent article 1 also has a waist elastic element 34 located in the back portion 7 close to the back edge 21 of the absorbent article 1.

The absorbent core 5 is formed with a sealing arrangement which is constituted by the two channel sealings 9, 10 and the two side seams 15, 16. The sealing arrangement is configured so that, in the crotch portion 8, the absorbent core 5 is divided into a centre segment 5a and two side segments 5b, 5c. More precisely, and as shown in FIG. 2, the centre segment 5a has a first width a1 and each side segment 5b, 5c has a second width a2. Also, a third width b1 is defined between the two channel sealings 9, 10. Furthermore, a fourth width b2 is defined between the first channel sealing 9 and the first side seam 15, and also between the second channel sealing 10 and the second side seam 16.

According to FIGS. 1 and 2, the absorbent component 5a, 5b 5c is configured so that the total amount of absorbent material of the centre segment 5a is generally equal to or greater than the total amount of absorbent material in each one of the side segments 5b, 5c. As will be described in greater detail below, the absorbent material may comprise a mixture of pulp material and superabsorbent material. Also, the ratio of the first width a1 and the third width b1 is greater than the ratio of the second width a2 and the fourth width b2. In practical terms, this means that the available space for expansion of the absorbent material in the centre segment 5a, during use of the absorbent article 1 in its wet condition, is less than the corresponding available space for each side segment 5b, 5c. This will lead to a situation in which the centre segment 5a will be stiffer (in its wet condition) than the side segments 5b, 5c. This means that any tendency in the crotch portion 8 of the absorbent article 1 to sag will be reduced, in particular in its wet condition.

The expression "generally equal" as used above for describing the amount of absorbent material in the centre segment 5a as compared with the side segments 5b, 5c should be interpreted in a manner wherein the amount of absorbent material could have a variation of approximately ±5% in any part of the crotch portion 8.

The absorbent component 5a,5b,5c in the crotch portion may be configured so that 33-41 weight % of the absorbent material is in the centre segment 5a, whereas 25-33 weight % is in each one of the side segments 5b, 5c. In this manner, the desired stiffness in the centre segment 5a may be obtained.

In summary, the absorbent core 5 comprises an absorbent component which in turn comprises the three above-mentioned segments 5a, 5b, 5c in the crotch portion 8 of the absorbent article 1. In the crotch portion 8, the absorbent component 5a, 5b, 5c comprises absorbent material-which may be in the form of pulp material and superabsorbent material. The pulp material may have a basis weight which is in the interval of 50-400 g/m² and the superabsorbent material may have a basis weight which is in the interval of 100-900 g/m².

The width of the centre segment is defined as (a1) and the absorbent component width is defined as (a3). The ratio of the width (a1) of the centre segment 5a and the width (a3) of the absorbent component 5a,5b,5c is 0.25-0.45.

Various types of materials may be used for the absorbent article 1. The topsheet 3 is arranged to face the wearer of the absorbent article 1 when worn. The topsheet 3 may be formed by a fluid permeable nonwoven fabric or film which is made of thermoplastic synthetic fibers. The topsheet 3 may be sufficiently liquid-permeable to allow discharged body fluids to penetrate through the thickness of the topsheet 3. Also, the topsheet 3 may be suitably manufactured from a material which is compliant and soft-feeling to the skin of the wearer. The topsheet 3 may consist of a single layer or have a laminate structure comprising a plurality of layers, for example, two or more layers. The layers may be made of the same material, or some or all the layers may be made of different materials.

The layer of the topsheet 3 or, for the case of a laminate structure, one, some, or all layers of the topsheet may be made of a single material or have plural portions made of different materials, e.g., within different parts of the wearer-facing surface of the topsheet. The layer of the topsheet 3 or, for the case of a laminate structure, one, some or all layers of the topsheet may be a nonwoven material, a perforated plastic film, a plastic or textile mesh, or a liquid permeable foam layer. The layer of the topsheet 3 or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers. The topsheet may have a basis weight in the range of 8-40 g/m². However, the disclosure is not limited to topsheets having this basis weight only.

Furthermore, the backsheet 4 may be constituted by a liquid-impermeable and breathable layer such as a polymeric film, for example a film of polyethylene or polypropylene. According to different embodiments, the materials which may be used for the backsheet 4 include thin and flexible fluid impermeable plastic films, or fluid impermeable nonwoven materials, fluid impermeable foams and fluid impermeable laminates. The backsheet 4 may be formed by a single layer, but may alternatively be formed by a multi-layered structure, i.e., a laminate, wherein at least one layer is fluid impermeable. Furthermore, the backsheet 4 may be elastic in any direction. Furthermore, the backsheet 4 may have a laminate structure comprising a liquid barrier sheet and a nonwoven layer arranged on top of each other (not shown in detail in the drawings), wherein the nonwoven layer is arranged at an outer side away from the wearer of the absorbent article 1 when worn.

The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials. The nonwoven layer may have a basis weight in the range of 5-40 g/m².

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers. The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo and/or mechanical bonding, such as thermo-sealing, ultrasonic bonding, such as ultrasonic welding, an adhesive or adhesives, stitching or the like. The liquid barrier sheet may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes.

Regarding the choice of materials for the various layers in the absorbent article, the materials may be chosen for the bonding process to form the channel sealings and side seams. For example, if ultrasonic welding is chosen for joining the upper and lower core cover sides, the chosen materials for the core cover may be adapted to form a secure bond during ultrasonic welding.

Furthermore, the absorbent core 5 is provided between the topsheet 3 and the backsheet 4 to absorb the liquid, such as urine or other bodily fluids, which has passed through the topsheet 3. The absorbent component 5a,5b,5c may be made of one layer, or two or more layers. The absorbent component 5a,5b,5c may comprise suitable amounts of superabsorbent material. Such superabsorbent material is well known in the field of absorbent articles, and is constituted by a water-swellable and water-insoluble material which is capable of absorbing large quantities of fluid upon formation of a hydrogel. The absorbent component may contain superabsorbent material in the form of fibers or particles of absorbent polymer material. For example, the superabsorbent material may be surface cross-linked, partially neutralized polyacrylates. The superabsorbent material, e.g., the superabsorbent fibers or particles, may be mixed with other absorbent or liquid uptake material or materials, such as cellulose fluff pulp, and/or arranged in pockets or layers in the absorbent core 5. The amount of superabsorbent material and pulp in the absorbent component 5a,5b,5c may be 0-50 weight % pulp fibers and 50-100 weight % superabsorbent material, or 0-30 weight % pulp fibers and 70-100 weight % superabsorbent material.

The absorbent component 5a,5b,5c may further comprise components for improving the properties of the absorbent core 5. For example, the absorbent component 5a,5b,5c may comprise a binder or binders, such as binder fibers.

The core cover 11,12 may be formed by a separate upper core cover 11 layer and a separate lower core cover 12 layer. However, the disclosure is not limited to a core cover comprising two separate core cover layers. The core cover 11,12 may also be of one single material layer. The absorbent component 5a,5b,5c may be enclosed by one core cover 11,12 layer folded in two, or enclosed by a continuous core cover sheet, thereby providing upper 11 and lower core cover 12 sides for wrapping the absorbent component 5a,5b, 5c. The basis weight of the core cover 11,12 material may be in the interval 5-20 g/m². The core cover 11,12 material may be made of thermoplastic polymer material. The core cover material may be nonwoven material. The nonwoven material may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

Furthermore, as known by the skilled person, the various layers of the absorbent article 1 may be attached by means of adhesive material. Such adhesive is not shown in the drawings.

One or more additional layers may be provided in the absorbent article 1. For example, an acquisition layer may be arranged between the absorbent core 4 and the topsheet 3. Such an additional layer may for example be in the form of an airlaid layer, a spunlace layer, a high-loft, foam or any other type of material layer which may be used in an absorbent article to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by means of pressure and vacuum.

According to an embodiment, the ratio of the first width a1 of the centre segment 5a and the third width b1, i.e., the distance between the channel sealings 9, 10 (i.e., a1/b1) is in the interval 0.75-0.91, such as 0.80-0.86. Furthermore, the ratio of the second width a2 of each side segment 5b, 5c and the fourth width b2, i.e., the distance between each channel sealing 9, 10 and its corresponding, adjacent side seam 11, 12 (i.e., a2/b2) is in the interval 0.57-0.71, such as 0.62-0.66. In this manner, the required stiffness of the centre segment 5a may be obtained.

In general, the article 1 is arranged so that the ratio of the first width a1 and the third width b1 is greater than the ratio of the second width a2 and the fourth width b2, i.e., $(a1/b1) > (a2/b2)$ Furthermore, the first, second, third and fourth widths a1, a2, b1, b2, respectively, may be configured so that:

$b1 < b2*2$ and $a1 < a2*2$

In addition to the arrangement of the first, second, third and fourth widths a1, a2, b1, b2, as described above, the absorbent article 1 is arranged to provide the desired stiffness of the centre segment 5a and the entire absorbent article 1 by the above-mentioned arrangement of the absorbent material in the absorbent core 5. This means that the centre segment 5a is configured for a stiffness in a wet condition which is greater than that of each side segment 5b, 5c. This also means that the absorbent component, i.e., consisting of the centre segment 5a and the side segments 5b, 5c, may be configured with an ability to expand on wetting and to display a first volume in dry condition and a second volume in completely expanded wet condition, the second volume being greater than the first volume.

With reference again to FIG. 1, it can be noted that each channel sealing 9, 10 may have a length l1 which corresponds to the longitudinal extension of the crotch portion 8. Each one of the channel sealings 9, 10 may have a length l1 which is between 5-50%, such as 10-50%, such as 28-38%, of the total length l of the absorbent article 1. Furthermore, each channel sealing 9, 10 may have a length l1 which is between 10-60%, such as between 20-60%, such as between 30-50%, of the length of the absorbent core 5.

A further parameter is the positioning of the channel sealings 9, 10 along the absorbent article 1 in its longitudinal direction. Such positioning may be defined by choosing a suitable value for the distance l2 between the front edge 19 of the article 1 and the front edge 20 of each channel sealing 9, 10. Obviously, this means that decreasing said distance l2 means that the distance l3 between the back edge 21 of the article 1 and the back edge 22 of the channel sealings 9, 10 will be increased, and vice versa.

The position of the channel sealings 9, 10 along the longitudinal direction of the absorbent article 1 may be chosen in a manner so that the distance l2 between the front edge 17 of the article 1 and the front edge 18 of each channel 9, 10 is between 15-40%, such as between 22-25%, of the total length l of the article 1.

As mentioned above, the absorbent core 5 is sandwiched between an upper core cover side 11 and a lower core cover side 12. The absorbent core 5 may be manufactured as a single layer which is wrapped in nonwoven material and positioned between the topsheet 3 and the backsheet 4 during manufacturing of the absorbent article 1.

Furthermore, the topsheet may comprise at least one additive material such as a skin care composition. The additive may be located on the parts of the topsheet covering the side segments 5b, 5c. An advantage with such an embodiment, is that the side segments 5b, 5c normally will be closer to the body of the wearer of the absorbent article 1 than the centre segment 5a.

According to what is known to the skilled person, the absorbent article 1 may additionally be provided with further components such as fastening tabs, elastic elements and other components which are commonly used in absorbent articles such as for example baby diapers or incontinence garments. Such additional components are not described in detail here.

Figure 3:
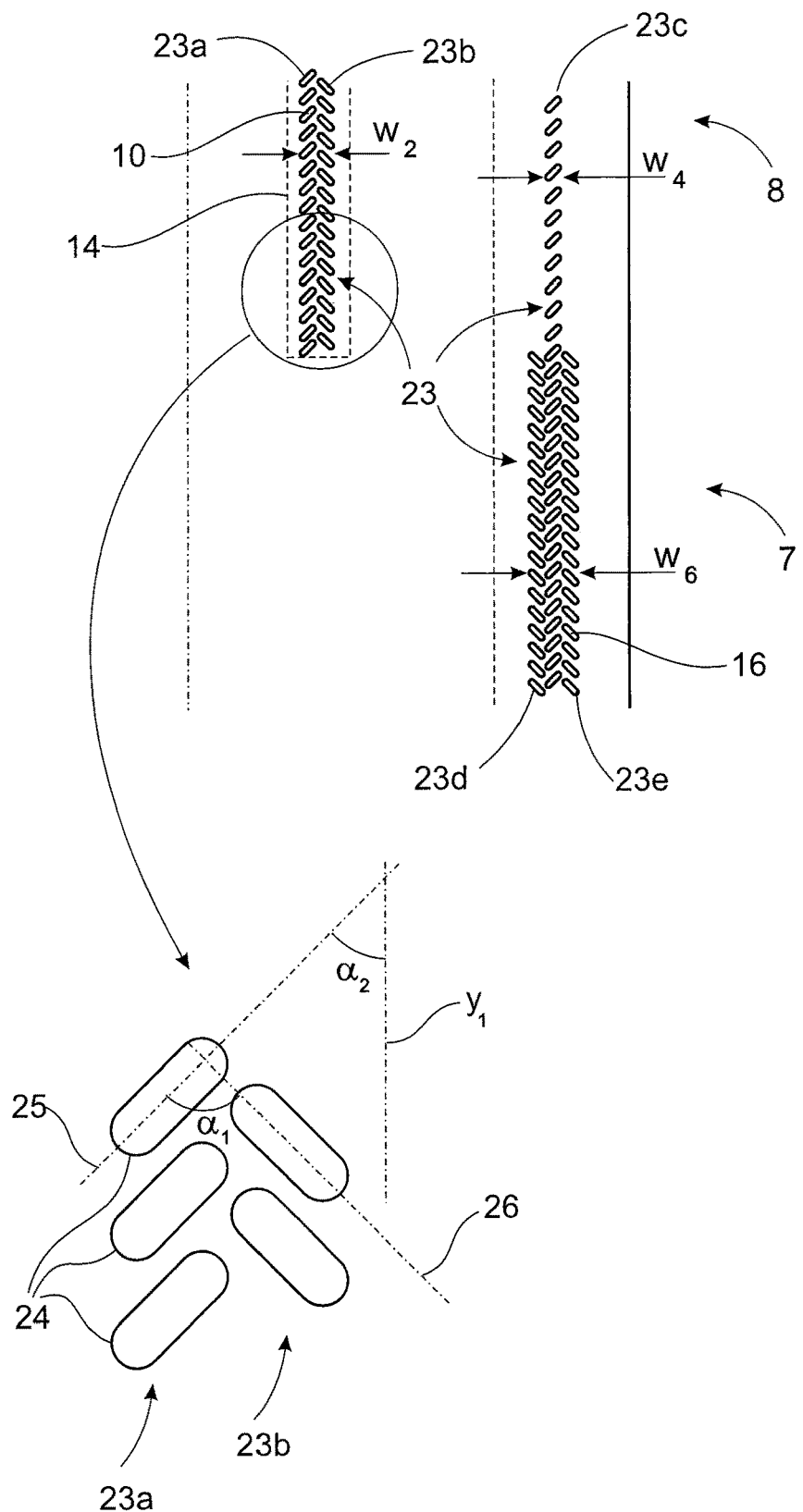
FIG. 3 shows a welding pattern which can be implemented in an exemplary embodiment of the disclosure.

With reference to FIG. 3, an absorbent core 5 is provided with a sealing arrangement 9, 10, 15, 16, i.e., comprising the above-mentioned channel sealings 9, 10 and the side seams 15, 16. As shown in FIG. 3, the side seams 15, 16 extend along the side edges 17, 18 of the core. The side seams 15,16 may define a first side seam width w3 and a second side seam width w4, respectively, along the crotch portion 8 of the absorbent article 1.

As shown in FIG. 3, the channel sealings 9, 10 may be generally straight and generally parallel to the longitudinal axis x1. Also, the side seams 15, 16 may be generally straight and generally parallel to the longitudinal axis x1.

Figure 4:
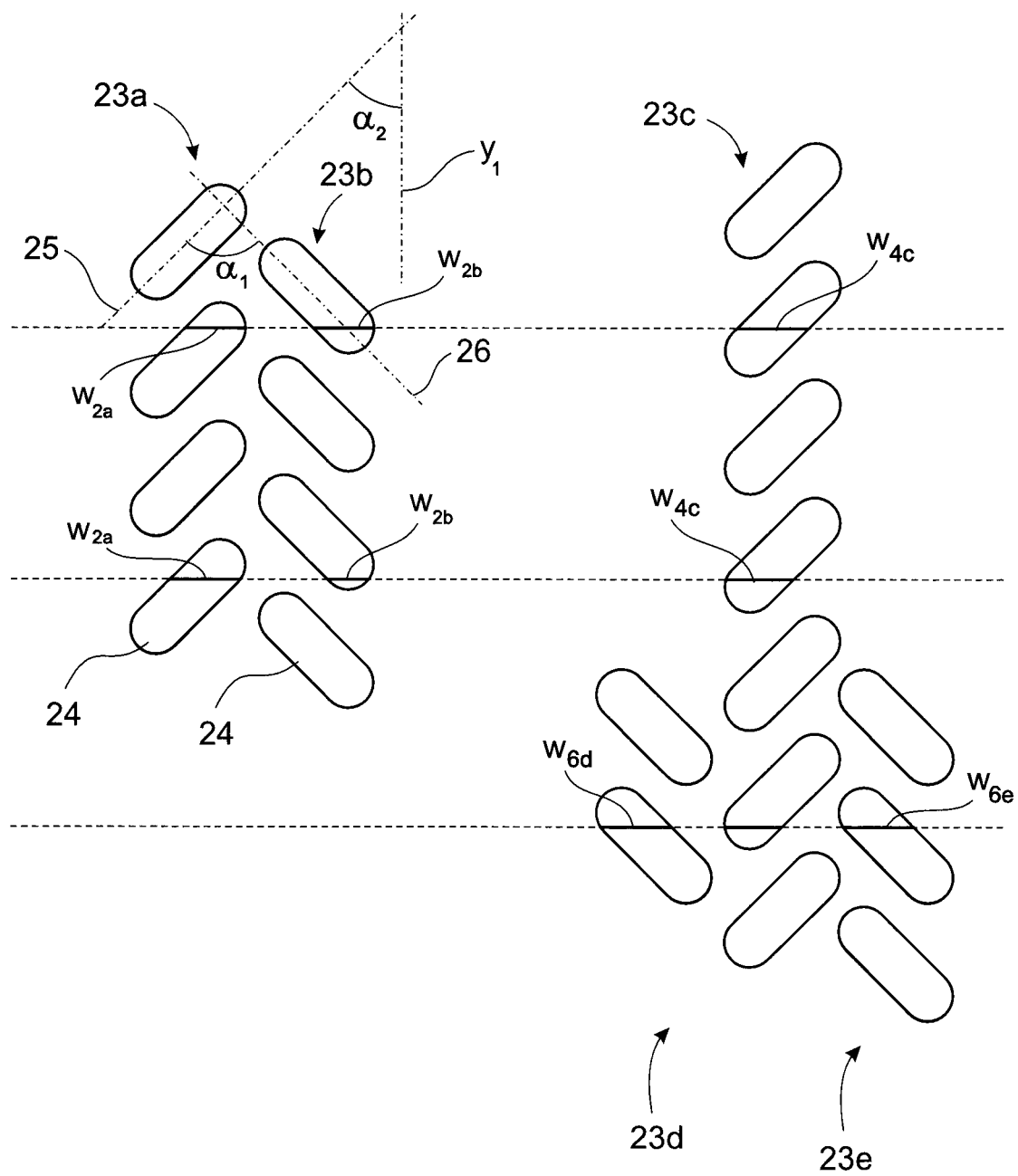
FIG. 4 shows a further view of a welding pattern.

With reference to FIG. 4, the sealing arrangement 9, 10, 15, 16 may be constituted by a welding pattern 23 produced by means of ultrasonic welding. The welding pattern 23 may comprise welding spots 24 which are arranged in the form of a first row 23a in which the welding spots 24 are arranged along a first axis 25. Also, a further number of welding spots 24 are arranged in the form of a second row 23b in which the welding spots 24 extend along a second axis 26. Furthermore, the first axis 25 and the second axis 26 extend in a manner so that they define a first angle $\alpha 1$ in relation to each other. In this manner, it can be ensured that the absorbent core 5 can be manufactured with a high level of material strength in both its longitudinal and transversal direction.

The welding spots 24 may be of generally rectangular, oval or oblong shape. Also, the above-mentioned first angle α1 may be in the interval of 45-100°. As shown in FIG. 4, the first angle α1 may be in the magnitude of 90°.

Also, as shown in FIG. 4, the first axis 25 may define an angle α2 with reference to said longitudinal axis y1 which is within the interval 30-60°.

FIG. 4 teaches one row 23c of welding spots in each side seam 15, 16 along the crotch portion 8, and three rows 23c, 23d, 23e of welding spots in each side seam 15, 16 along the front portion 6 and the back portion 7, respectively. Also, each side seam 15, 16 may define a fifth side seam width w5 and a sixth side seam width w6 along the front portion 6 and back portion 7, respectively.

As shown in FIGS. 3 and 4, the width w2 of the first row 23a and the second row 23b may be defined as an "effective" width in the sense that it is equal to the sum of an effective width w2a of a welding spot 24 in the first row 23a and an effective width w2b of a welding spot 24 in the second row 23b. Each "effective width" can be defined as the length of a welding spot 24 in a transverse direction of the article 1, as indicated in FIG. 4. Similarly, the effective width w4c and w6c, respectively, of the third row 23c of welding spots 24 is also shown in FIG. 4. The effective width of the third row 23c in the crotch portion 8 is the length w4c of a welding spot 24 in said transverse direction, as indicated in FIG. 4. Also, the effective width of the side seam 16 outside the crotch portion 8 (as also indicated in FIG. 1) i. e the combined effective width of the three rows 23c, 23d, 23e forming the side seam 16 is the sum of the lengths w6d, w6c, w6e in said transverse direction, as shown in FIG. 4.

The sum of the effective channel sealing widths w1, w2 and the first and second side seam widths w3, w4, w5, w6 in a transversal direction of the article 1 may be generally constant along the longitudinal length of the core 5. This is particularly advantageous in a manufacturing process involving ultrasonic welding of the channels sealings 9, 10 and the side seams 15, 16, since the manufacturing process can be arranged so that a generally constant energy is required as the ultrasonic welding of the channels sealings 9, 10 and side seams 15, 16 is produced along the longitudinal direction of the core 5.

The disclosure may be varied within the scope of the appended claims. For example, the materials and dimensions used for the different layers forming the absorbent article 1 may be varied, as indicated above. The absorbent article may further include standing gathers, side panels, fastening systems etc. as known to the skilled man in the art and depending of the type of absorbent article intended.

The invention claimed is:

1. An absorbent article comprising an absorbent core sandwiched between a liquid-permeable topsheet and a liquid-impermeable backsheet, said article being arranged along a longitudinal axis and a transversal axis extending in a perpendicular direction in relation to the longitudinal axis, said article comprising a front portion, a back portion and a crotch portion and said absorbent core comprises an absorbent component having a width in the transversal direction and the absorbent component is enclosed by a core cover comprising an upper side and a lower side, wherein:
   two channel sealings are extending along said longitudinal axis in said crotch portion for joining said upper and lower side of the core cover;
   the absorbent component has one centre segment having a first width between the channel sealings, and two side segments outside each channel sealing;
   the absorbent component is formed so that the total amount of absorbent material in the centre segment is generally equal to, or greater than, the total amount of absorbent material in each one of the side segments;
   the channel sealings and the centre segment are generally parallel to the longitudinal axis;
   the absorbent component is configured with an ability to expand on wetting and displaying a first volume in dry condition and a second volume in completely expanded wet condition, the second volume being greater than the first volume, and the core cover, which is arranged around the absorbent component, defines and limits an expansion space for the centre segment so that the centre segment is prevented from reaching complete expansion to the second volume on wetting;
   the ratio of the first width of the centre segment and the width of the absorbent component, in dry condition, is 0.25-0.45;
   the article further comprises two side seams along sides of said core;
   each of the two side segments has a second width;
   a third width is defined between the channel sealings; and
   for each of the two side segments, a fourth width is defined between a channel sealing and a side seam, and the ratio of the first width to the third width is in an interval of 0.75-0.91 and the ratio of the second width to the fourth width is in an interval of 0.57-0.71.

2. The absorbent article according to claim 1, wherein the ratio of the width of the centre segment and the width of the absorbent component, in dry condition, is 0.30-0.40.

3. The absorbent article according to claim 1, wherein the width of the centre segment, in dry condition, is 25-35 mm.

4. The absorbent article according to claim 1, wherein the centre segment after wetting has a greater stiffness than in dry condition and thus forms a forming element in the absorbent article.

5. The absorbent article according to claim 1, wherein the thickness of the absorbent component in dry condition measured with an applied pressure of 0.5 kPa is 3.0-5.5 mm.

6. The absorbent article according to claim 1, wherein the article also has leg elastic elements extending along each longitudinal side edge of the absorbent article, and wherein the leg elastic elements have a greater length in the longitudinal direction than the length of the channel sealings in the longitudinal direction.

7. The absorbent article according to claim 6, wherein the leg elastic elements, in the longitudinal direction, are extending also along a part of the front portion and the back portion.

8. The absorbent article according to claim 7, wherein the leg elastic elements have a greater extension in the back portion than in the front portion.

9. The absorbent article according to claim 6, wherein the ratio of the width of the centre segment and the distance in the transversal direction between the leg elastics is 0.10-0.30.

10. The absorbent article according to claim 1, wherein the article also has a waist elastic element located in the back portion close to the back edge of the absorbent article.

11. The absorbent article according to claim 1, wherein the absorbent component in the crotch portion is configured so that 33-41 weight % of the absorbent material is in the centre segment and 25-33 weight % of the absorbent material is in each one of the side segments.

12. The absorbent article according to claim 1, wherein said absorbent material in said absorbent component, at least in said crotch portion, comprises pulp material and superabsorbent material, said pulp material having a basis weight which is in the interval of 50-400 g/m2 and said superabsorbent material having a basis weight which is in the interval of 100-900 g/m2.

13. The absorbent article according to claim 1, wherein said absorbent component, at least in said crotch portion, is constituted by 50-100 weight % superabsorbent material and 0-50 weight % pulp material, or 70-100 weight % superabsorbent material and 0-30 weight % pulp material.

14. The absorbent article according to claim 1, wherein each channel sealing has a length which is between 5-50% of the total length of the article.

15. The absorbent article according to claim 1, wherein the position of the channel sealings along the longitudinal direction of the article is arranged so that the distance between the front edge of the article and the front edge of each channel is between 15-40% of the total length of the article.

16. The absorbent article according to claim 1, wherein said absorbent component is constituted by one single absorbent component layer being wrapped in a core cover having an upper and lower side.

17. The absorbent article according to claim 1, wherein said channel sealings are positioned within two corresponding channels which constitute sections of the absorbent core which are generally free from absorbent material.

18. The absorbent article according to claim 1, wherein the sealing arrangement is constituted by a welding pattern produced by a thermo and/or mechanical sealing method.

19. Absorbent core for an absorbent article, said absorbent core comprising an absorbent component having a width in the transversal direction and the absorbent component is enclosed by a core cover comprising an upper side and a lower side, wherein:

two channel sealings are extending along said longitudinal axis in said crotch portion for joining said upper and lower side of the core cover, the absorbent component has one centre segment having a first width between the channel sealings and two side segments outside each channel sealing and the absorbent component is formed so that the total amount of absorbent material in the centre segment is generally equal to, or greater than, the total amount of absorbent material in each one of the side segments and wherein the channel sealings and the centre segment are generally parallel to the longitudinal axis;

the absorbent component is configured with an ability to expand on wetting and displaying a first volume in dry condition and a second volume in completely expanded wet condition, the second volume being greater than the first volume, and the core cover, which is arranged around the absorbent component, defines and limits an expansion space for the centre segment so that the centre segment is prevented from reaching complete expansion to the second volume on wetting;

the ratio of the first width of the centre segment and the width of the absorbent component, in dry condition, is 0.25-0.45;

the absorbent core further comprises two side seams along sides of said absorbent core;

each of the two side segments has a second width;

a third width is defined between the channel sealings; and for each of the two side segments, a fourth width is defined between a channel sealing and a side seam, and the ratio of the first width to the third width is in an interval of 0.75-0.91 and the ratio of the second width to the fourth width is in an interval of 0.57-0.71.

20. The absorbent article according to claim 1, wherein the channel sealings are parallel to one another along an entirety of the channel sealings between respective front and rear edges of the channel sealings.

21. The absorbent core according to claim 19, wherein the channel sealings are parallel to one another along an entirety of the channel sealings between respective front and rear edges of the channel sealings.

* * * * *